United States Patent
Roh et al.

(10) Patent No.: US 6,288,272 B1
(45) Date of Patent: Sep. 11, 2001

(54) CONTINUOUS PROCESS FOR PREPARING OPTICALLY PURE (S)-3,4-DIHYDROXYBUTYRIC ACID DERIVATIVES

(75) Inventors: Kyoung Rok Roh; Jongpil Chun; Yik-haeng Cho; Young Mi Park; Hosung Yu; Dae Il Hwang, all of Daejeon (KR)

(73) Assignee: Samsung Fine Chemicals Co., Ltd. (KR)

( * ) Notice: Subject to any disclaimer, the term of this patent is extended or adjusted under 35 U.S.C. 154(b) by 0 days.

(21) Appl. No.: 09/359,676

(22) Filed: Jul. 23, 1999

(30) Foreign Application Priority Data

Jul. 24, 1998 (KR) .................................................. 98-29912

(51) Int. Cl.⁷ .......................... C07C 69/66; C07C 51/00; C12P 29/00; C12P 19/00; C12P 19/60
(52) U.S. Cl. .......................... 562/515; 562/515; 560/186; 435/64; 435/72; 435/75
(58) Field of Search .......................... 562/515; 560/186; 435/64, 72, 74

(56) References Cited

U.S. PATENT DOCUMENTS

| | | |
|---|---|---|
| 3,791,865 | 2/1974 | Hurst et al. |
| 3,922,200 | 11/1975 | Guillaume et al. |
| 3,986,890 | 10/1976 | Richter et al. |
| 4,138,484 | 2/1979 | Fuxe . |
| 4,447,532 | 5/1984 | Coker et al. |
| 4,612,284 | 9/1986 | Pickens et al. |
| 4,855,232 | 8/1989 | Takasaki . |
| 5,292,939 | * 3/1994 | Hollingsworth . |
| 5,319,110 | 6/1994 | Hollingsworth . |
| 5,374,773 | 12/1994 | Hollingsworth . |
| 5,506,353 | 4/1996 | Subramaniam . |
| 5,808,107 | * 9/1998 | Hollingsworth . |

FOREIGN PATENT DOCUMENTS

| | | |
|---|---|---|
| 451142 A2 | 10/1991 | (EP) . |
| 64-13069 | 1/1989 | (JP) . |
| 4-149151 | 5/1992 | (JP) . |
| 4-158795 | 6/1992 | (JP) . |
| 6-172256 | 6/1994 | (JP) . |
| WO 93/06826 | 4/1993 | (WO) . |
| WO 94/05639 | 3/1994 | (WO) . |
| WO 98/04543 | 2/1998 | (WO) . |
| WO99/05092 | 2/1999 | (WO) . |

OTHER PUBLICATIONS

Enzymic Conversion of Startch into D–Glucose Syrup Using Glucoamylase and Pullulanase, B.E. Norman, 1994, "Methods in Carbohydrate Chemistry".*
Organic Chemistry, 6th Edition, Morrison and Boyd.*
J. Am. Chem. Soc., 105, 5925–5926 (1983).
J. Am. Chem. Soc., 117, 1181 (1995).
J. Am. Chem. Society, 2245–2247 (1953).
J. Chem. Soc., 1924–1931 (1960).
J. Chem. Soc., 1932–1938 (1960).
J. Am. Chem. Soc., 1431–1435 (1955).
J. Am. Chem. Soc., 81, 3136 (1959).
Bull. Chem. Soc. Jpn., 61, 2025 (1988.
J. Org. Chem., 50, 1144 (1985).
Tetrahedron Letter, 46, 4277 (1990).
Tetrahedron Letter, 33, 2279 (1992).
Tetrahedron Lett., 507 (1992).
Tetrahedron Lett., 31, 267–270 (1990).
Chem. Lett., 1389–1392 (1984).
J. Res. Natl. Bur. Standards., vol. 32, No. 2, p. 45 (1944).
Can. J. Chem., 65, 195 (1987).
Carbohyd. Res., 11, 17–25 (1969).
Starch 41 Nr. 8, S. 303–309 (1989).
Synthesis, 597–613 (1997).
J. Chromatography, 549, 113–125 (1991).
Encyclopedia of Chemical Technology 3th ed. 491–507.
Methods Carbohydr. Chem., 10, 231–239 (1994).
Methods Carbohydr. Chem., 10, 245–248 (1994).

* cited by examiner

*Primary Examiner*—Paul J. Killos
*Assistant Examiner*—John N Calve
(74) *Attorney, Agent, or Firm*—Finnegan, Henderson, Farabow, Garrett & Dunner, LLP

(57) ABSTRACT

The present invention relates to a continuous process for preparing optically pure (S)-3,4-dihydroxybutyric acid derivatives expressed by the following Formula 1 and more particularly, to the continuous process which enables preparing optically pure (S)-3,4-dihydroxybutyric acid derivatives economically in large quantities, by:

(a) Preparing α-(1,4) linked oligosaccharide having adequate sugar distribution by reacting amylopectin which is easily available from natural product with enzyme under a specific condition; and (b) Performing oxidatioin by running basic anion exchange resin with an oxidant to give (S)-3,4-dihydroxybutyric acid-anion exchange resin complex, dissociating the (S)-3,4-dihydroxybutyric acid from anion exchange resin complex and esterification sequentially under a specific condition.

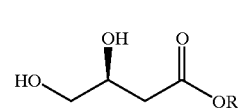

(1)

wherein Represents linear or branched alkyl group with 1~5 carbon atoms.

14 Claims, 3 Drawing Sheets

CONTINUOUS PROCESS FOR PREPARING OPTICALLY PURE (S)-3,4-DIHYDROXYBUTYRIC ACID DERIVATIVES

BACKGROUND OF THE INVENTION

1. Field of the Invention

The present invention relates to a continuous process for preparing optically pure (S)-3,4-dihydroxybutyric acid derivatives expressed by the following Formula 1 and more particularly, to the continuous process which enables preparing optically pure (S)-3,4-dihydroxybutyric acid derivatives economically in large quantities, by:

(a) Preparing α-(1,4) linked oligosaccharide having adequate sugar distribution by reacting amylopectin which is easily available from natural product with enzyme under a specific condition; and (b) Performing oxidation by running basic anion exchange resin with an oxidant to give (S)-3,4-dihydroxybutyric acid-anion exchange resin complex, dissociating the (S)-3,4-dihydroxybutyric acid from anion exchange resin complex and esterification sequentially under a specific condition.

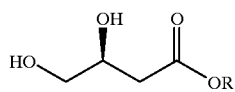

(1)

wherein, R represents linear or branched alkyl group with 1~5 carbon atoms.

Description of the Related Arts (S)-3,4-Dihydroxybutyric acid derivatives and (S)-3-hydroxy-γ-butyrolactone are used as synthetic intermediates for preparing various chiral compounds. For example, it is well known that they act as key intermediates for preparing neuromeidator (R)-GABOB [Tetrahedron, 46, 4277(1990)], treatment for hyperlipemia (Atorvastatin; HMG-CoA reductase inhibitor) [Tetrahedron Lett., 33, 2279(1992)], (S)-oxiracetam which is improvement agent in brain metabolism [International patent publication WO93/06,826], L-carnitin which is health supplement agent [International patent publication WO99/05,092], (S)-3-hydroxytetrahydrofuran [*J Am. Chem. Soc.*, 117, 1181(1995); International patent publication WO94/05,639] which is an essential intermediate of AIDS drug (Agenerase; HIV protease inhibitor), (S)-monobetalactam [Japanese patent publication 64-13,069(1989)], ester of (S)-3-hydroxy-4-bromobutyric acid [Japanese patent publication 4-149,151(1992); Japanese patent publication 6-172,256(1994)], potentiating intermediate of satiety agent [*Bull. Chem. Soc. Jpn.*, 61, 2025(1988)] and neuroleptic drug [USP 4,138,484] and useful intermediates in synthetic efforts towards natural products [*J. Org. Chem.*, 50, 1144 (1985), *Can. J. Chem.*, 65, 195 (1987), *Tetrahedron Lett.*, 507 (1992)]. Optical purity is the most important factor in preparing these chiral compounds.

The conventional techonologies for preparing (S)-3,4-dihydroxybutyric acid derivatives and (S)-3-hydroxy-γ-butyrolactone, which are useful for preparing the said chiral compounds, are explained in detail hereunder.

Methods of preparing (S)-3-hydroxybutyric acid derivatives from the enzymatic or catalytic reduction of β-ketoester were known [*J. Am. Chem. Soc.*, 105, 5925~5926(1983); *Teterahedron Lett.*, 31, 267~270(1990); European patent publication 452,143A2]. These methods have difficulty in that the prochiral center should be reduced to one-side to generate chiral center and expensive metal catalyst should be used.

A technology preparing ester of (S)-3,4-dihydroxybutyric acid and (S)-3-hydroxy-γ-butyrolactone by selective reduction of (L)-malic acid ester was known [*Chem. Lett.*, 1389~1392(1984); U.S. Pat. No. 5,808,107]. This technology has disadvantage in that reduction should be performed selectively to only one of the two ester functional groups.

Many methods of preparing (S)-3,4-dihydroxybutyric acid derivatives and (S)-3-hydroxy-γ-butyrolactone from carbohydrate have been reported.

A technology preparing isosaccharinic acid (B) or (S)-3,4-dihydroxybutyric acid (C) is reported [*J. Chem. Soc.*, 1924~1931(1960)] by alkaline degradation of carbohydrate containing glucose substituent in the 4-position, such as 4-O-methyl-(D)-glucose, maltose, amylose and cellulose, elimination of C-4 substituent as leaving group, forming dicarbonyl compound (A; 4-deoxy-2,3-hexodiulose), and reacting the formed dicarbonyl compound with base as shown in Scheme 1. However, the yield of (S)-3,4-dihydroxybutyric acid is low.

Scheme 1

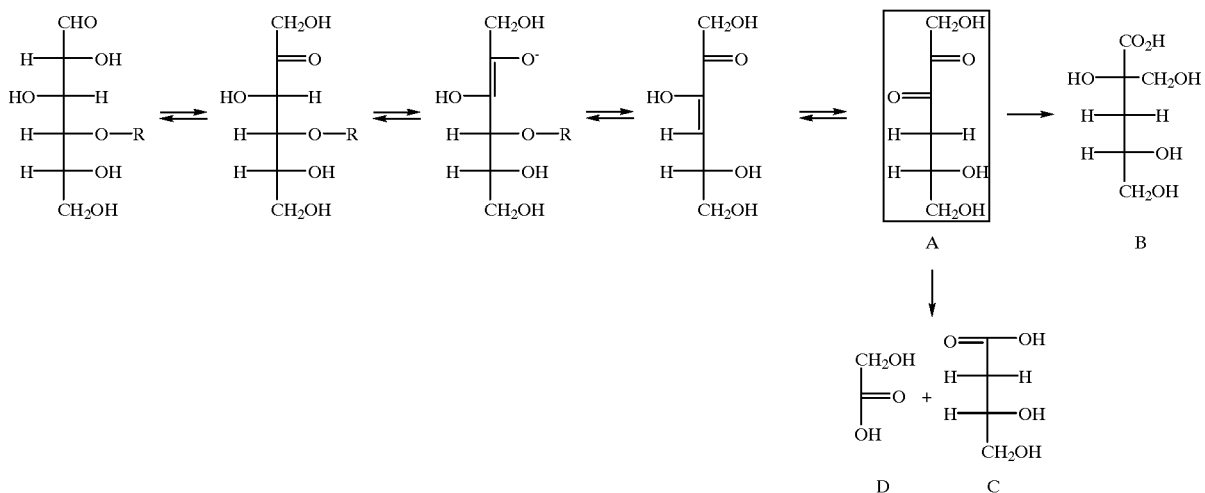

R = 1,4-linked glucosan

Also, it has been reported that (S)-3,4-dihydroxybutyric acid (C) and glycolic acid (D) were obtained as major products by forming dicarbonyl compound (A) from alkaline degradation of carbohydrate containing glucose substituent in the 4-position, and separating the formed dicarbonyl compound (A) and reacting it with hydrogen peroxide [*J. Chem. Soc.*, 1932~1938(1960)]. This method has a serious problem that the product exists as small amounts of isomers due to tautomerization and a mixture of cyclic compounds and hydrates derived from dicarbonyl compound (A). So, the dicarbonyl compound (A) cannot be separated in good yields from the reaction mixture. Another problem is that the prepared (S)-3,4-dihydroxybutyric acid is degraded to formic acid and glycolic acid due to the overoxidation.

A similar technology for preparing (S)-3,4-dihydroxybutyric acid from carbohydrate either using base only or using oxygen in base was known. It proposed that the dicarbonyl compound (A) was a synthetic intermediate for (S)-3,4-dihydroxybutyric acid as shown in the Scheme 1. But the yield was reported to be as low as about 30% [*J. Res. Natl. Blir. Stand.*, 32, 45(1944); *J. Am. Chem. Soc.*, 2245~2247(1953); *J. Am. Chem. Soc.*, 1431~1435(1955); *Carbohyd. Res.*, 11, 17~25(1969); *J. Chromatography*, 549, 113~125(1991)]. In these methods, (S)-3,4-dihydroxybutyric acid is produced with various kind of mixtures including glycolic acid (D), isosaccharinic acid (B), formic acid, ketone, diketone and glyceric acid. Since the yield of (S)-3,4-dihydroxybutyric acid is very low, these methods are also considered as not suitable for industrial use.

A method for preparing (S)-3,4-dihydroxybutyric acid from disaccharide (lactose) using base and oxidant has been reported [International patent publication WO98/04543]. In this work, (S)-3,4-dihydroxybutyric acid was cyclized to (S)-3-hydroxy-γ-butyrolactone under the reaction condition and purified by protection of the two hydroxy groups to acetonide ester compound, methyl (S)-3,4-O-isopropylidene-3,4-dihydroxybutanoate, which was recyclized to (S)-3-hydroxy-γ-butyrolactone under acidic media.

Preparing methods of (S)-3,4-dihydroxybutyric acid including the process of alkaline oxidation of carbohydrate containing glucose substituent in the 4-position have been known [U.S. Pat. No. 5,292,939, 5,319,110 & 5,374,773 (1994)]. In these methods, dicarbonyl compound (A) intermediate is formed at first, oxidized to (S)-3,4-dihydroxybutyric acid (C) and glycolyic acid (D). However, optical purity, the most important physical property of chiral compounds, is not mentioned at all. Also, purification of target compounds is very difficult, considering the reaction mechanism. In the case of disaccharides such as maltose or lactose, only one sugar unit in the disaccharide forms (S)-3,4-dihydroxybutyric acid and the other sugar unit functions as leaving group, so that the target product and leaving group coexist as 1:1 mixture. Accordingly, it is very difficult to separate and purify (S)-3,4-dihydroxybutyric acid or (S)-3-hydroxy-γ-butyrolactone from the reaction mixture. The theoretical mass conversion obtainable is 28.3 wt %. In other words, 28.3 g of (S)-3-hydroxy-γ-butyrolactone can be obtained from 100 g of disaccaride. For polysaccharides, such as maltodextrin, starch and cellulose, mentioned in the above patents, the (1,4) and/or (1,6) glucose units are linked complexly like nets. The problem is that the step-by-step oxidation proceeding from the reducing end units comprising (1,4) linkage terminates at (1,6) linkage unit. Therefore no more target product is formed. Also, the polysaccharides are degraded by overoxidation of reducing end units to complex acid mixtures containing formic acid, oxalic acid, glycolic acid and erythronic acid [*J. Am. Chem. Soc.*, 81, 3136(1959); Starch 41 Nr. 8, S. 303~309(1989); *Synthesis*, 597~613(1997)].

There was an attempt to improve the yield of (S)-3,4-dihydroxybutyric acid or (S)-3-hydroxy-γ-butyrolactone for polysaccharide by degradation of higher-molecular sugars to relatively lower-molecular sugars through acid or base hydrolysis. Though the reactivity by this method is increased to a degree, (1,4) linkage and (1,6) linkage are not hydrolyzed selectively to afford random distribution. Accordingly, there is a fundamental problem in preparing (S)-3,4-dihydroxybutyric acid and its derivatives in high yield [*Encyclopedia of Chemical Technology*, 3th ed. 492~507].

Regarding the preparation of (S)-3-hydroxy-γ-butyrolactone using (1,4) linked polysaccharide, the step-by-step oxidation proceeds continuously from the reducing-end units to non-reducing end units to afford (S)-3,4-dihydroxybutyric acid until the last chain unit (a leaving group) is remained. Namely, if (1,4) linked polysaccharide is used as a source material for preparing (S)-3-hydroxy-γ-butyrolactone, the theoretical mass conversion obtainable is 63 wt %, about two times more compared with the method using disaccharide. In other words, 63 g of (S)-3-hydroxy-γ-butyrolactone can be obtained from 100 g of (1,4)-linked polysaccharide. Also, since the small amount of leaving group is produced in the reaction mixture compared with disaccharide, the target product is easily purified. Therefore, the use of (1,4) linked polysaccharide promises the enhanced productivity.

However, regarding conventional polysaccharides, the target product and by-products (acids such as formic acid, oxalic acid, glycolic acid and erythronic acid) is formed competitively in the step-by-step oxidation due to the compact structure having random (1,4) linkage and (1,6) linkage. Thus, selective degradation technique of polysaccharide to a suitable sugar distribution range having (1,4) linkage is required.

On the other hand, there have been many reports of transforming higher-molecular sugars to lower-molecular sugars using biological enzymatic treatment process for industrial use.

The reported technologies include preparing glucose, maltose and ethanol through enzymatic treatment of starch [U.S. Pat. No. 3,791,865(1974); U.S. Pat. No. 3,922,200 (1975); U.S. Pat. No. 4,855,232(1989): Japanese patent publication 4-158,795(1992); *Methods Carbohydr. Chem.*, 10, 231~239(1994); *Methods Carbohydr. Chem.*, 10, 245~248(1994)], and preparing maltodextrin with adequate dextrose equivalent (DE) [U.S. Pat. No. 3,986,890(1976); U.S. Pat. No. 4,447,532(1984); U.S. Pat. No. 4,612,284 (1986); U.S. Pat. No. 5,506,353(1996)]. In these references, through the degradation or transformation of high molecular polysaccharides, it is converted to adequate materials for medicines, food additives and diagnostic reagents.

But, method for preparing (1,4) linked oligosaccharides suitable for the mass production of (S)-3,4-dihydroxybutyric acid derivatives by biological treatment of higher molecular polysaccharides with enzymes is not known at present.

SUMMARY OF THE INVENTION

The inventors of the present invention made intensive efforts to develop a continuous method for preparing optically pure (S)-3,4-dihydroxybutyric acid derivatives from commercially available amylopectin with ease. As a result, a process which enables preparing optically pure (S)-3,4- dihydroxybutyric acid derivatives economically in large quantities is found by preparing oligosaccharide with structural specificity which can minimize formation of by-products from amylopectin by enzymatic reaction, performing oxidation by running basic anion exchange resin with an oxidant to give (S)-3,4-dihydroxybutyric acid-anion exchange resin complex, dissociating the (S)-3,4-dihydroxybutyric acid from anion exchange resin complex, and esterification sequentially under a specific condition. Because glucose generated from the above oxidation as a leaving group does not adsorbed on anion exchange resin, it can be easily removed by washing anion exchange resin with water compared with conventional oxidation methods using inorganic base. Also, anion exchange resin used above oxidation can be simultaneously regenerated by dissociation process. Therefore, it can be re-used for oxidation of oligosaccharide. This is one of superior advantages of the present invention.

Accordingly, an object of this invention is to provide a continuous method for preparing optically pure (S)-3,4-dihydroxybutyric acid derivatives in high yield by preparing oligosaccharide with structural specificity by enzymatic reaction, performing oxidation by running basic anion exchange resin with an oxidant to give (S)-3,4-dihydroxybutyric acid-anion exchange resin complex, dissociating the (S)-3,4-dihydroxybutyric acid from anion exchange resin complex and esterification sequentially without additional purification of intermediates.

DETAILED DESCRIPTION OF THE INVENTION

Figure 1A:
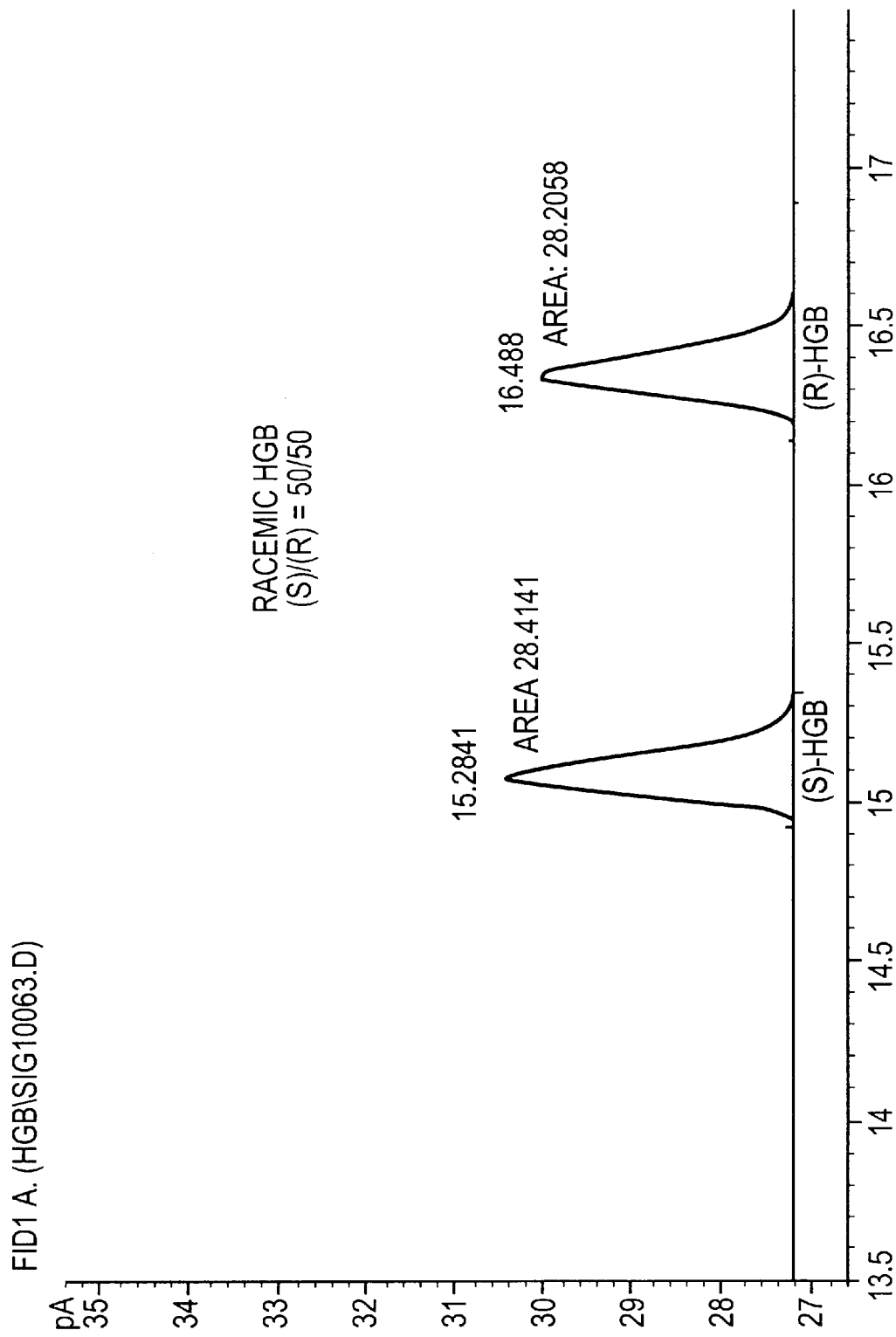
FIG. 1a represents the optical purity analysis results by gas chromatography (GC) of racemic 3-hydroxy-γ-butyrolactone.

The present invention is characterized by comprising the following steps:

(a) Enzymatic reaction of amylopectin to a-(1,4) linked oligosaccharide expressed by the Formula 2;

(b) Oxidation of the oligosaccharide by running basic anion exchange resin with an oxidant to afford (S)-3, 4-dihydroxybutyric acid expressed by the Formula 3; and (c) Subsequent esterification with alcohol in the presence of an acid catalyst to afford ester of (S)-3,4-dihydroxybutyric acid expressed by the Formula 1;

(2)

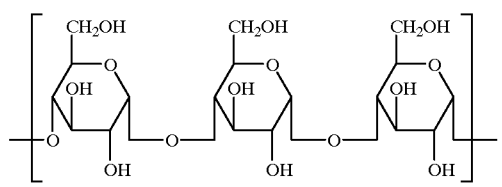

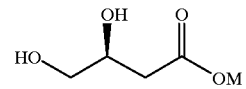

(3)

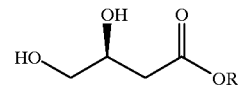

(1)

Wherein, M represents hydrogen, alkali metal or alkali earth metal atom; R represents linear or branched alkyl group with 1~5 carbons. The detailed description of the present invention is given hereunder. The fundamental inventive concept of the present invention is selective degradation of α-(1,4) linkage and α-(1,6) linkage within amylopectin using specific enzymes, i.e., transforming amylopectin to α-(1,4) linked oligosaccharide with the optimal sugar distribution for preparing the target compound. And subsequent oxidation by running basic anion exchange resin with an oxidant to give (S)-3,4-dihydroxybutyric acid removing simultaneously a by-product, glucose, easily and effectively and esterification is performed for preparing optically pure (S)-3,4-dihydroxybutyric acid derivatives.

Namely, focusing on the specificity of enzymes, amylopectin is degraded sequentially with specific enzymes to α-(1,4) linked oligosaccharide, and optically pure (S)-3,4-dihydroxybutyric acid derivatives are prepared from the transformed oligosaccharide by oxidation running basic anion exchange resin to give (S)-3,4-dihydroxybutyric acid removing simultaneously a by-product, glucose, easily and esterification sequentially in high yield. Optical purity of the desired product prepared by a sequential method is over 99.9%ee.

Oligosaccharide used in the present invention is prepared with biological enzymatic treatment of amylopectin, and amylopectin is commercially available with ease. Especially, since amylopectin is highly soluble in water or in buffer solution of pH 4.0~8.0, used as reaction solvent for enzymatic reaction of the present invention, the relative reactivity to enzyme is greatly increased compared with other polysaccharides such as starch and cellulose. Thus, the same is very effective material for preparing of oligosaccharide having suitable sugar distribution for the preparation of (S)-3,4-dihydroxybutyric acid derivatives.

When using pullulanase as an enzyme for selective degradation of α-(1,6) linkage in amylopectin, it causes the solubility problem of amylopectin and reduced enzyme activity. So, rather than using pullulanase only, α-amylase was used to improve reactivity in degrading amylopectin to a suitable sugar distribution, and then pullulanase was used. However, in this case, activity of the remaining α-amylase persists and thus amylopectin is degraded excessively, so that the desired oligosaccharide is not formed. Accordingly, a technology of inactivating the remaining α-amylase before the pullulanase reaction was introduced.

The detailed explanation of the preparation process of this invention is as follow. It comprises; 1) a step preparing oligosaccharide with characteristic α-(1,4) linkage expressed in Formula 2 by selective degradation of amylopectin using biological treatment of specific enzymes, 2) a step preparing optically pure (S)-3,4-dihydroxybutyric acid through oxidation running basic anion exchange resin with an oxidant, 3) subsequent esterification with alcohol in the presence of an acid catalyst to afford ester of (S)-3,4-dihydroxybutyric acid. Especially, the preparation process of this invention is characterized by preparing (S)-3,4-dihydroxybutyric acid derivatives in the same reactor without additional purification of the intermediates (oligosaccharide and (S)-3,4-dihydroxybutyric acid).

The enzymatic reaction of the present invention uses α-amylase and pullulanase sequentially. α-Amylase degrades α-(1,4) linkage and pullulanase degrades α-(1,6) linkage selectively.

The superiority of the present invention lies in that optically pure (S)-3,4-dihydroxybutyric acid derivatives are prepared in high yield under a mild reaction condition by using enzymes selectively degrading α-(1,4) linkage or α-(1,6) linkage, while the chemical hydrolysis method has no selectivity.

The enzymatic reaction of the present invention is performed in water or buffer solution of pH 4.0~8.0 at 40~120° C. α-Amylase is used in the range of 0.001~10 wt % of amylopectin, and enzymatic reaction of α-amylase is performed for 30 min~4 hr, and then remaining α-amylase is inactivated. Inactivation is performed under acidic (pH 2.0~4.5) and high temperature (60~150° C.) conditions and maintained for 10 min 4 hr. In the enzymatic reaction of pullulanase, pullulanase is used in the range of 0.001~10 wt % of amylopectin, and most of the oligosaccharides distribute within 3~50 glucose units by 10~40 hr of the pullulanase enzymatic treatment. Reducing end units and molecular weight distribution of the prepared oligosaccharide is analyzed from reducing end units and dextrose equivalent analysis by an optical analyzer, HPLC analysis, and gel permeation chromatography (GPC) analysis.

The oligosaccharide is obtained from the selective enzymatic reaction and has distribution mostly between 3~50 glucose units, and preferably 5~50 glucose units. Since most of the glucose units are linked with α-(1,4) linkage, (S)-3,4-dihydroxybutyric acid derivatives can be obtained in high yield through continuous sequential reactions with minimizing the by-products (e.g., acid mixtures of formic acid, oxalic acid, glycolic acid and erythronic acid). Furthermore, the obtained (S)-3,4-dihydroxybutyric acid derivatives were identified to be optically very pure (>99.9%ee).

Oxidation of oligosaccharide is performed by running basic anion exchange resin with an oxidant to afford (S)-3,4-dihydroxybutyric acid absorbed on the resin in the column. Aqueous alkali metal or alkaline earth metal solution is used for dissociating the absorbed (S)-3,4-dihydroxybutyric acid.

Oxidation of oligosaccharide explained above is in the following scheme 2.

Scheme 2

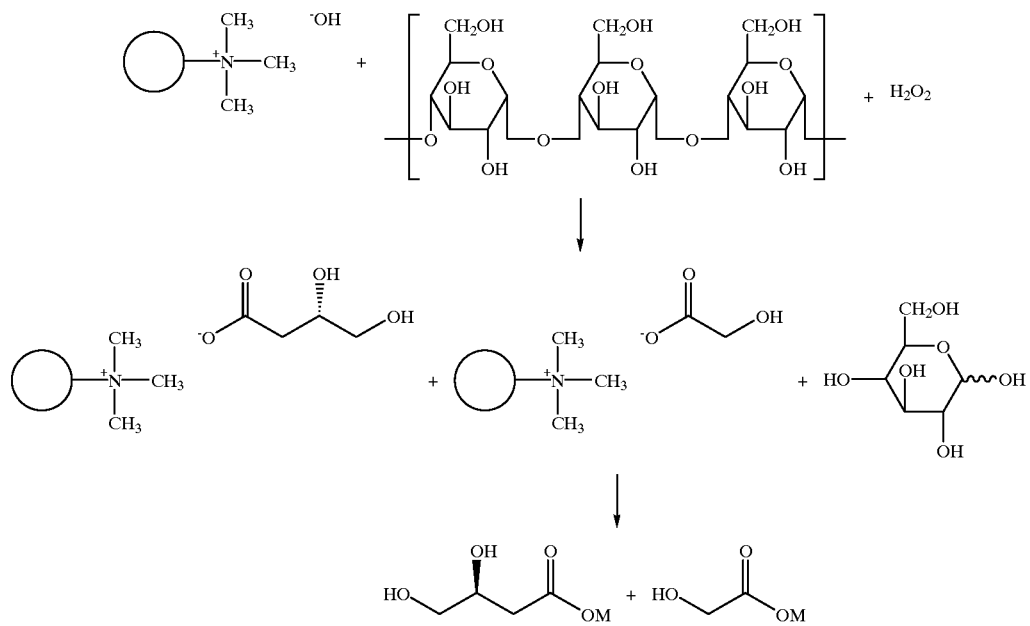

whererin, ●—represents supporter; M represents hydrogen, alkali metal or alkaline earth metal atom.

In oxidation of oligosaccharide of scheme 2, basic anion exchange resin acts as a base and oligosaccharide is oxidized by an oxidant ot produce (S)-3,4-dihydroxybutyric ascid and glycolic acid which are absorbed on the anion exchange resin. The glucose (a leaving group) of oligosaccharide stays in the reaction solution.

After oxidation, anion exchange resin is washed with water to remove a leaving group, glucose, and other by-products and then aqueous alkali metal or alkaline earth metal solution is eluted to dissociate (S)-3,4-dihydroxybutyric acid with a rate of 2 BV/hr. One of advantagers of this invention is regeneration of the basic anion exchange resin used for oxidation by dissociation process, which can be re-used for oxidation step semipermanently.

Oxidation of oligosaccharide is performed at 30~65° C. for 6~36 hr. Hydrogen peroxide, alkali metal peroxides, alkaline earth metal peroxides and alkyl hydroperoxides are used for the oxidants, and hydrogen peroxides is the most preferable. The oxidant is used in the range of 1~3 equivalents per molar glucose unit of amylopectin. The basic anion exchange resin is used for a base and strong basic anion exchange resin with quaternary ammonium hydroxide is preferable. The basic anion exchange resin is used in the range of 2~4 equivalents per molar glucose unit of amylopectin.

Esterification of the present invention is performed in the presence of acid catalyst using alcohol as both a reaction solvent and reagent in the range of 30~80° C. Inorganic acids such as hydrochloric acid, sulfuric acid, phosphoric acid and nitric acid, and organic acids such as fluoroalkylsulfonic acid, aralkylsulfonic acid, hydrate of aralkylsulfonic acid and trifluoroacetic acid are used as acid catalyst. Linear or branched alcohol with 1~5 carbon atoms is used for the alcohol.

In order to compare the preparation yields depending on the source material of oxidation, the prepared (S)-3,4-dihydroxybutyric acid derivatives were cyclized (S)-3-hydroxy-γ-butyrolactone as follows [Refer to Experimental example 1]. (S)-3,4-dihydroxybutyric acid derivatives were cyclized in the presence of acid catalyst by agitating the same in the range of 30~80° C. to obtain (S)-3-hydroxy-γ-butyrolactone for 2~5 hr. Inorganic acids such as hydrochloric acid, sulfuric acid, phosphoric acid and nitric acid, and organic acids such as fluoroalkylsulfonic acid, aralkylsulfonic acid, hydrate of aralkylsulfonic acid and trifluoroacetic acid are used as acid catalyst. As a result, if maltose (disaccharide) or lactose (disaccharide) obtained from cheese by-product is used as the source material, the theoretical mass conversion yield of (S)-3-hydroxy-γ-butyrolactone is not more than 28.3 wt % of the source material weight used. On the other hand, if amylose (α-(1,4) linked polysaccharide) with more than 50 glucose units is used, the theoretical mass conversion yield of (S)-3-hydroxy-γ-butyrolactone is equal to that of amylopectin. But the double helix structure due to very strong intramolecular hydrogen bond limits the step-by-step oxidation, so the yield becomes very low. However, by using oligosaccharide of the present invention is used as source material, the yield of (S)-3-hydroxy-γ-butyrolactone is very high as 56.6 wt % of the source material weight used.

Therefore, the present invention provides advantages of simple preparing routes and enables the reactions to proceed continuously and thereby produces (S)-3,4-dihydroxybutyric acid derivatives economically in large quantities.

As explained above, the present invention is excellent in that the low reactivity of amylopectin to oxidation is overcome by transforming amylopectin to oligosaccharide with the application of specific enzymes. Furthermore, by-product formation is minimized and by performing oxidation with basic anion exchange resin, it can be easily removed by simple process (washed with water). Thus, (S)-3,4-dihydroxybutyric acid can be prepared in high yield with very simple purification process.

The following examples are intended to be illustrative of the present invention and should not be construed as limiting the scope of this invention defined by the appended claims.

EXAMPLE 1

Preparation of Methyl (S)-3,4-dihydroxybutanoate

10 L of water and 5 kg of dried amylopectin were put into a 50 L reactor. After heating the reactor to 55° C., 12 g of α-amylase (BAN; EC 3.2.1.1 from *Bacillus licheniformis*, Novo Nordisk) was added. After heating this reaction solution to 75° C., the same was stirred for 2 hours at the same temperature. 5 mL of 0.1N HCI solution was added to adjust the pH of the reaction solution to 3.0~3.5, and then the same was stirred for 1 hr at 90° C. to inactivate the remaining α-amylase. After slowly cooling the reaction mixture to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stifed for 22 hr at the same temperature.

Basic anion exchange resin (Amberlite IRA 402 OH; 0.95 eq/L, Rohm and Hass, 75 L) containing quarternary ammonium hydroxide solution was placed in other 100 L reactor and heated to 50° C. To the reaction solution were added dropwise a solution of oligosaccharide prepared by the above enzyme reaction and 30% of hydrogen peroxide for 24 hr and the mixture was stirred for 1 hr at the same temperature. The reaction solution was cooled to room temperature and poured into the column. 100 kg of water was eluted to remove a leaving group, glucose, and other side products, and 100 kg of 3 wt % of NaOH aqueous solution was eluted to obtain (S)-3,4-dihydroxy-butyric acid sodium salt. The prepared (S)-3,4-dihydroxybutyric acid sodium salt was identified using NMR analysis. $^1$H-NMR ($D_2O$, ppm) δ 2.27 (dd, 1H), 2.39 (dd, 1H), 3.41 (dd, 1H), 3.51 (dd, 1H) 3.8~3.9 (m, 1H).

The reaction solution was concentrated, and 10 L of methanol was added. Sulfuric acid were added to adjust the pH to 4~5, and then the same was stirred for 3 hr at 50° C. Sodium carbonate was added to neutralize the solution, and the same was filtered to remove the by-product, and then methanol was concentrated to obtain methyl (S)-3,4-dihydroxybutanoate. The formation of methyl (S)-3,4-dihydroxybutanoate (conversion ratio: 91%) was identified through NMR analysis by the comparison of internal standard. $^1$H-NMR ($CDCl_3$, ppm) δ 6 2.5 (dd, 2H), 3.5 (dd, 1H), 3.6 (dd, 1H), 3.7 (s, 3H), 4.1 (m, 1H).

EXAMPLE 2

Preparation of (S)-3-hydroxy-γ-butyrolactone

10 L of water and 5 kg of dried amylopectin were put into a 50 L reactor. After heating the reactor to 55° C., 12 g of α-amylase (Teramyl; EC 3.2.1.1 from *Bacillus amyloliquefaciens*, Novo Nordisk) was added. After heating this reaction solution to 85° C., the same was stirred for 2 hr at the same temperature. 5 mL of 0.1N HCI solution was added to adjust the pH 3.0~3.5, and then the same was stirred for 1 hr at 90° C. to inactivate the remaining (α-amylase. After slowly cooling the reaction to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. A column with 10 cm in diameter and 100 cm in height was packed with basic anion exchange resin (Amberlite IRA 402 OH; 0.95 eq/L, Rohm and Hass, 75 L) and heated to 50° C. Oligosaccharide prepared by the above enzyme reaction and 30% of hydrogen peroxide solution (5.25 kg) were added dropwise for 24 hr. The reaction in the column was cooled down to room temperature. 100 kg of water was eluted to remove a leaving group, glucose, and other side products, and 110 kg of 3 wt % of NaOH aqueous solution was eluted to dissociate the absorbed (S)-3,4-dihydroxybutyric acid. The prepared (S)-3,4-dihydroxybutyric acid sodium salt was identified using NMR analysis. $^1$H-NMR ($D_2O$, ppm) δ 2.27 (dd, 1H), 2.39 (dd, 1H), 3.41 (dd, 1H), 3.51 (dd, 1H), 3.8~3.9 (m, 1H).

The reaction solution was concentrated, and 10 L of methanol was added. In this solution, methanesulfonic acid was added to adjust the pH to 4~5, and then the same was stirred for 3 hr at 50° C. After cooling, sodium carbonate was added to neutralize the solution, and the same was filtered to remove the by-product, and then methanol was concentrated to obtain methyl (S)-3,4-dihydroxybutanoate. Formation of methyl (S)-3,4-dihydroxybutanoate (conversion ratio: 92%) was identified using NMR analysis by comparing with the internal standard. $^1$H-NMR (CDCl$_3$, ppm) δ 2.5 (dd, 2H), 3.5 (dd, 1H), 3.6 (dd, 1H), 3.7 (s, 3H), 4.1 (m, 1H).

The prepared methyl (s)-3,4-dihydroxybutanoate was cyclized at 65° C. under reduced pressure by adding 0.5 wt % of concentrated HCl without any separation. The resultant solution was dissolved in ethyl acetate and the same was neutralized with sodium carbonate. After filtering and concentrating the same, (S)-3-hydroxy-γ-butyrolactone (2.83 kg, 56.6 wt % of the amylopectin weight used) was obtained. $^1$H-NMR (CDCl$_3$, ppm) δ 2.28 (dd, 1H), 2.74 (dd, 1H), 4.13 (dd, 1H), 4.32 (dd, 1H), 4.4~4.5 (m, 1H).

EXAMPLE 3

Preparation of (S)-3-hydroxy-γ-butyrolactone

As in the Example 2, however, using 1 wt % of methanesulfonic acid rather than concentrated HCl in the cyclization of the prepared methy (S)-3,4-dihydroxybutanoate, the same was cyclized at 65° C. under reduced pressure. The resultant solution was dissolved in ethyl acetate and the same was neutralized with sodium carbonate. After filtrating and concentrating the same, (S)-3-hydroxy-γ-butyrolactone (2.80 kg, 56 wt % of the amylopectin weight used) was obtained. 1H-NMR (CDCl$_3$, ppm) δ 2.28 (dd, 1H), 2.74 (dd, 1H), 4.13 (dd, 1H), 4.32 (dd, 1H), 4.4~4.5 (m, 1H).

EXAMPLE 4

Preparation of Methyl (S)-3,4-dihydroxybutanoate

As in the Example 1, however, using t-butylhydroperoxide (4.16 kg) rather than H$_2$O$_2$ for the oxidant, methyl (S)-3,4-dihydroxybutanoate was obtained. The formation of methyl (S)-3,4-dihydroxybutanoate (conversion ratio: 91%) was identified using NMR analysis by comparison with internal standard. $^1$H-NMR (CDCl3, ppm) δ 2.5 (dd, 2H), 3.5 (dd, 1H), 3.6 (dd, 1H), 3.7 (s, 3H), 4.1 (m, 1H).

COMPARATIVE EXAMPLE 1

Preparation of (S)-3-hydroxy-γ-butyrolactone from Starch

20 L of water and 5 kg of dried starch were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.1 kg, 22.0 wt % of starch weight used).

COMPARATIVE EXAMPLE 2

Preparation of (S)-3-hydroxy-γ-butyrolactone from Starch

10 L of 0.5N HCl solution and 5 kg of dried starch were put into a 50 L reactor, and the starch was hydrolyzed for 20 min at 100° C. After cooling the solution to 20° C., the same was neutralized with 100 mL of 40% NaOH solution and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.22 kg, 24.4 wt % of starch weight used).

COMPARATIVE EXAMPLE 3

Preparation of (S)-3-hydroxy-γ-butyrolactone from Amylose

20 L of water and 5 kg of dried amylose were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in the Example 2 to obtain (S)-3-hydroxy-γ-butyrolactone (1.35 kg, 27.0 wt % of amylose weight used).

EXPERIMENTAL EXAMPLE 1

Comparison of (S)-3-hydroxy-γ-butyrolactone Yield Depending on the Source Material For the reaction solutions containing each of the carbohydrates shown in Table 1, oxidation, esterification and cyclization were performed as in the Example 2 to obtain (S)-3-hydroxy-γ-butyrolactone. The yields of (S)-3-hydroxy-γ-butyrolactone are shown in Table 1.

TABLE 1

| Source material (5 kg) | Product (wt % compared with source material weight) |
| --- | --- |
| Oligosaccharide of the present invention (Example 2) | 2.83 kg (56.6 wt %) |
| Polysaccharide  Amylopectin | 1.01 kg (20.2 wt %) |
| Amylose | 1.35 kg (27.0 wt %) |
| Disaccharide (maltose)[a] | 1.19 kg (23.7 wt %) |

[a]Examples 1 & 2 of USP 5,292,939, 5,319,110 & 5,374,773

Table 1 shows that for disaccharide the relative mass conversion yield is low as 23.7 wt %. On the other hand, if amylopectin to oligosaccharide with specific enzyme treatment, the relative mass conversion yield is enhanced to 56.6 wt %, almost two times compared with disaccharide. If amylopectin is not treated with enzymes, the relative mass conversion yield is relatively low as 20.2 wt %.

EXPERIMENTAL EXAMPLE 2

Optical Purity Analysis of (S)-3-hydroxy-γ-butyrolactone (S)-3-Acetoxy-γ-butyrolactone was synthesized by the following method in order to analyze optical purity of (S)-3-hydroxy-γ-butyrolactone prepared from the present invention and the conventional preparing method.

102 mg (1 mmol) of (S)-3-hydroxy-γ-butyrolactone prepared from each method was dissolved in 3 mL of methylene chloride, and 0.4 mL (5 mmol) of pyridine and 0.47 mL (5 mmol) of acetic anhydride were added to the same. After 3 hr, the reaction was quenched with 1N HCl. (s)-3-Acetoxy-γ-butyroiactone was extracted with the methylene chloride. After work up, the same was purified with silica gel column chromatography. The obtained (S)-3-acetoxy-γ-butyrolactone was dissolved in methylene chloride, and 0.5

° C. was taken with syringe for GC analysis. The result is shown in the following Table 2 and FIGS. 1a~1c.

TABLE 2

| Source Material | Optical Purity |
| --- | --- |
| Disaccharide (maltose)[a] | 94% ee |
| Oligosaccharide of the present invention (Example 2) | 99.9% ee |

[a] Examples 1 & 2 of USP 5,292,939, 5,319,110 & 5,374,773

Figure 1B:
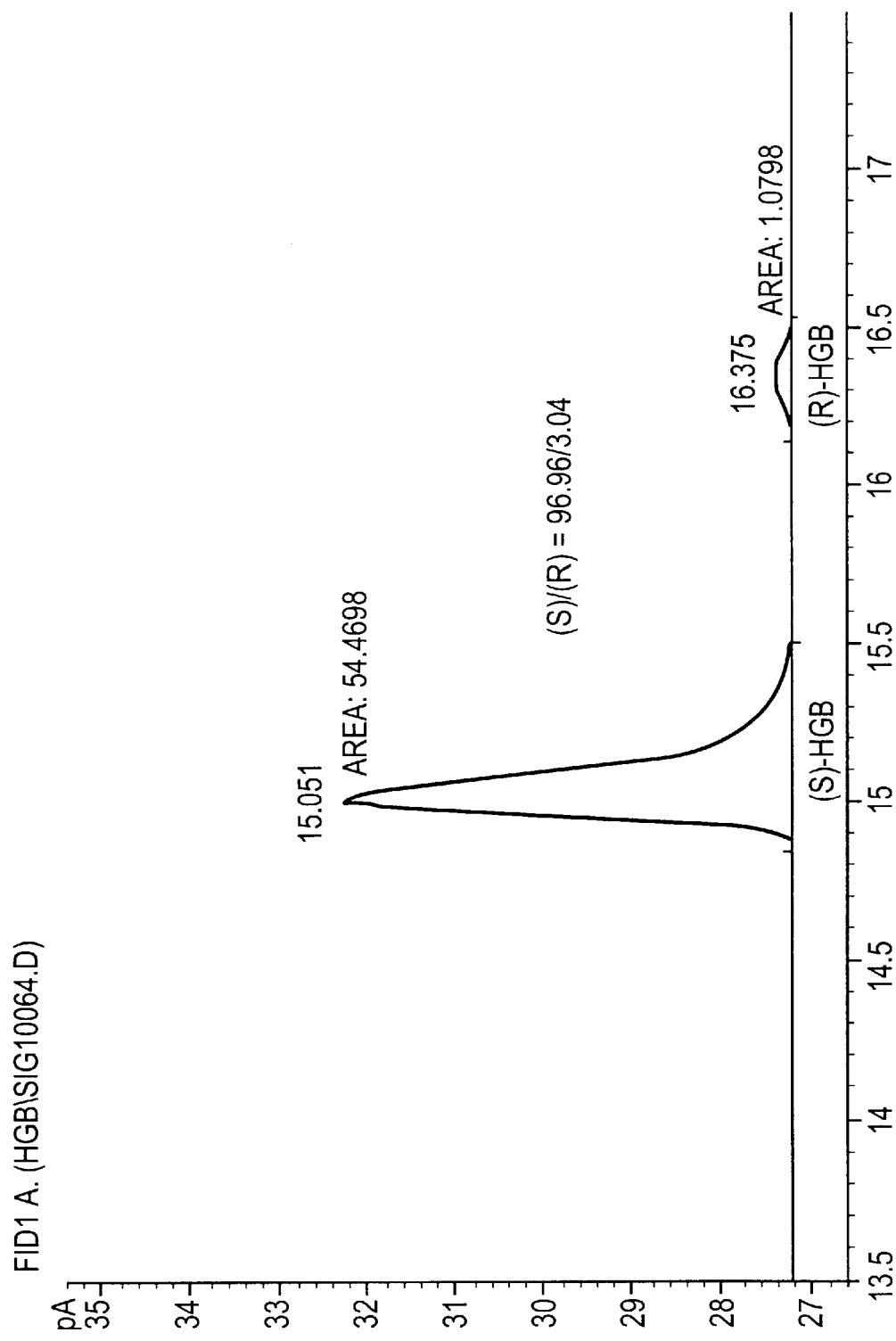
FIG. 1b represents the optical purity analysis results by gas chromatography (GC) of 3-hydroxy-γ-butyrolactone prepared from disaccharide of the conventional method.
Figure 1C:
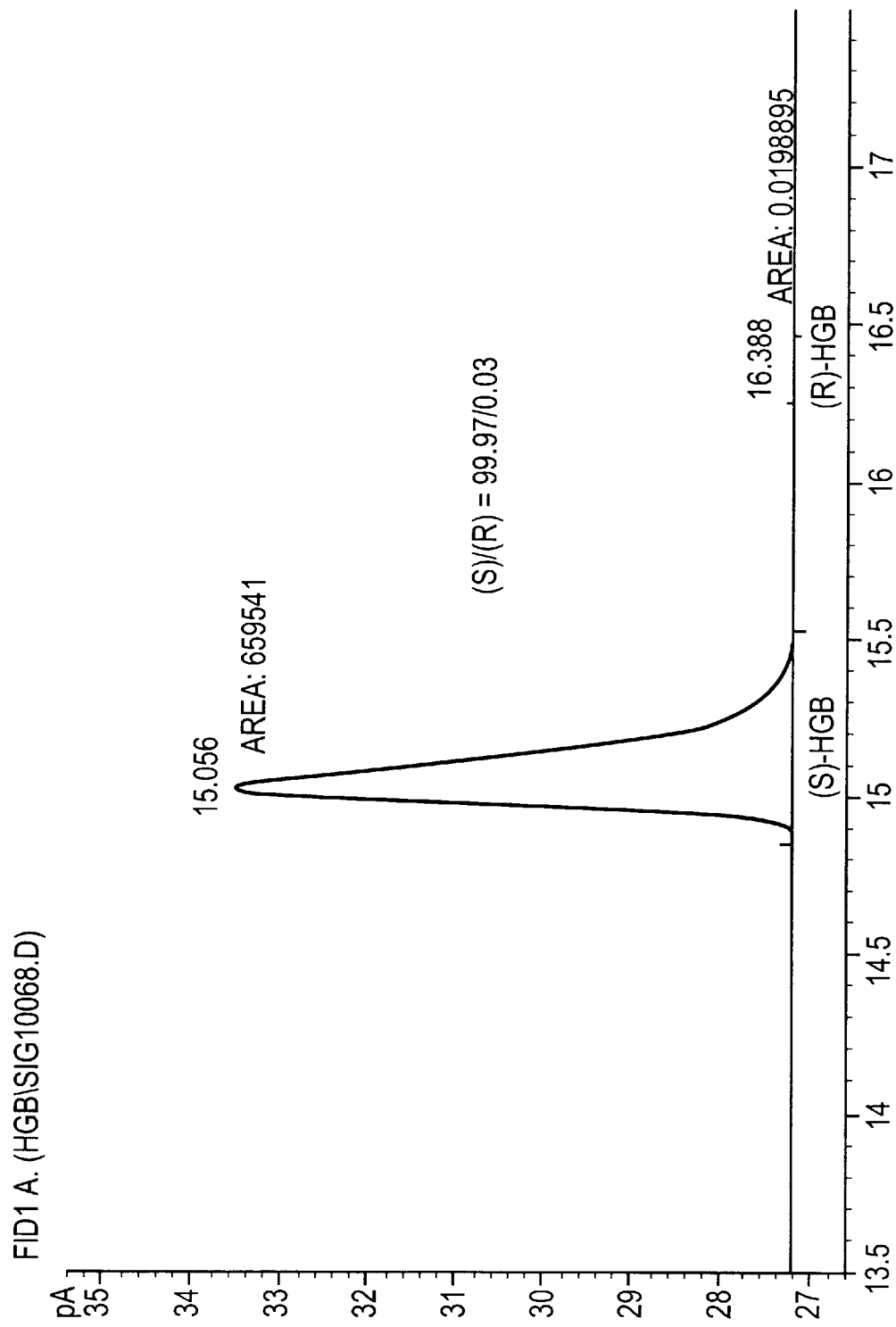
FIG. 1c represents the optical purity analysis results by gas chromatography (GC) of 3-hydroxy-γ-butyrolactone prepared from oligosaccharide of the present invention.

To improve the medicinal efficiency and minimize the side effect, more than 99.5%ee of high optical purity is required for chiral compounds. Table 2 and FIGS. 1a~1c show that the optical purity of (S)-3-hydroxy-γ-butyrolactone prepared from the present invention is very high as 99.9%ee. So, the same is very useful for the intermediates of other chiral compounds. The results are illustrated in FIGS. 1a, 1b, and 1c, respectively.

As described above, the preparing method of the present invention provides continuous method for production of (S)-3,4-dihydroxybutyric acid derivatives in a large quantities by preparing oligosaccharide with structural specificity which minimize formation of by-products form amylopectin, and performing oxidation running basic anion exchange resin with an oxidant to make easy removal of by-products without additional separation and purification.

Additionally, amylopectin as the source material is easily available form natural product with a low price compared with lactose and maltose and provides optically pure form. Use of oligosaccharide prepared from amylopectin provides that productivity is two times more compared with use of disaccharide.

Therefore, the present invention has overcome the disadvantage of using expensive metal catalyst for selective asymmetric reduction, and enables easy preparation from inexpensive natural product having optically pure chiral center, thereby the industrial utility as chiral intermediates of various medicine can be maximized. Furthermore, the relative mass conversion yield is almost double almost doubled compared with disaccharides.

What is claimed is:

1. A continuous process for producing optically pure (S)-3,4-dihydroxybutyric acid derivatives expressed by the following Formula 1 from polysaccharide source, which comprises the following steps:

(a) Enzymatic reaction of amylopectin to α-(1,4) linked oligosaccharide expressed by the Formula 2;
   (b) Oxidation of the oligosaccharide by running basic anion exchange resin with an oxidant to afford (S)-3,4-dihydroxybutyric acid expressed by the Formula 3; and
   (c) Subsequent esterification with alcohol in the presence of an acid catalyst to afford ester of (S)-3,4-dihydroxybutyric acid expressed by the Formula 1.

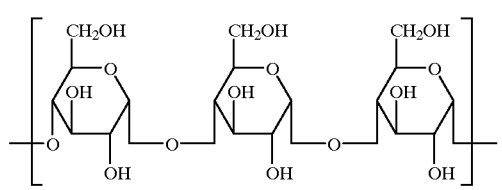

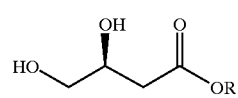

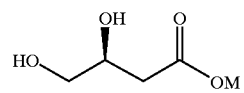

wherein, M represents hydrogen, alkali metal or alkali earth metal atom; R represents linear or branched alkyl group with 1~5 carbon atoms.

2. The continuous process according to claim 1, wherein the said oligosaccharide prepared by enzymatic reaction has the 3~50 glucose units.

3. The continuous process according to claim 1, wherein the said oxidation is performed in the range of 30~65° C.

4. The continuous process according to claim 1, wherein the oxidant used in the said oxidation is selected from hydrogen peroxide, alkali metal peroxide, alkaline earth metal peroxide and alkylhydroperoxide.

5. The continuous process according to claim 4, wherein the said oxidant is hydrogen peroxide.

6. The continuous process according to claim 4, wherein the said oxidant is t-butylhydroperoxide.

7. The continuous process according to claim 1 or claim 4, wherein the said oxidant is used in the range of 1~3 equivalents per molar glucose unit of amylopectin.

8. The continuous process according to claim 1, wherein the basic anion exchange resin used in the said oxidation is a strong basic anion exchange containing quarternary ammonium functional group.

9. The continuous process according to claim 1 or claim 8, wherein the said basic anion exchange resin is used in the range of 2~4 equivalents per molar glucose unit of amylopectin.

10. The continuous process according to claim 1, wherein the said anion exchange resin after oxidation is eluted with 2~50 wt % of aqueous alkali metal or alkaline earth metal solution to obtain (S)-3,4-dihydroxybutyric acid.

11. The continuous process according to claim 10, wherein the said aqueous solution is sodium hydroxide.

12. The continuous process according to claim 1, wherein the acid catalyst used in the said esterification is an inorganic acid selected from hydrochloric acid, sulfuric acid, phosphoric acid and nitric acid.

13. The continuous process according to claim 1, wherein the acid catalyst used in the said esterification is an organic acid selected from fluoroalkylsulfonic acid, aralkylsulfonic acid, hydrate of aralkylsulfonic acid and trifluoroacetic acid.

14. The continuous process according to claim 1, wherein the said esterification is performed in the range of 30~80° C.

* * * * *

UNITED STATES PATENT AND TRADEMARK OFFICE
CERTIFICATE OF CORRECTION

PATENT NO.    : 6,288,272 B1
DATED         : September 11, 2001
INVENTOR(S)   : Kyoung Rok Roh et al.

Page 1 of 1

It is certified that error appears in the above-identified patent and that said Letters Patent is hereby corrected as shown below:

<u>Title page,</u>
Item [57], ABSTRACT,
Line 18, change "Represents" to -- R represents --.

<u>Column 14, claim 7,</u>
Line 34, change "4, wherein" to -- 4, wherein --.

Signed and Sealed this

Twelfth Day of March, 2002

*Attest:*

JAMES E. ROGAN
*Director of the United States Patent and Trademark Office*

*Attesting Officer*